United States Patent [19]

Yoon et al.

[11] Patent Number: 5,704,943
[45] Date of Patent: Jan. 6, 1998

[54] LIGATING INSTRUMENT WITH MULTIPLE LOOP LIGATURE SUPPLY AND METHODS THEREFOR

[76] Inventors: InBae Yoon, 2101 Highland Ridge Dr., Phoenix, Md. 21131; Cynthia D. Yoon, 622 W. 114th St., Apt. 61A, New York, N.Y. 10025

[21] Appl. No.: 533,504

[22] Filed: Sep. 25, 1995

[51] Int. Cl.$^6$ .................................. A61B 17/10
[52] U.S. Cl. ..................... 606/139; 606/144; 606/148
[58] Field of Search ........................... 606/139, 146, 606/102, 113, 144, 148, 143

[56] References Cited

U.S. PATENT DOCUMENTS

| | | |
|---|---|---|
| 2,012,776 | 5/1935 | Roeder . |
| 2,227,270 | 1/1940 | Moore . |
| 2,610,631 | 11/1952 | Caliccchio . |
| 2,856,933 | 1/1958 | Hildebrand et al. . |
| 3,033,204 | 5/1962 | Wood . |
| 3,580,256 | 5/1971 | Wilkinson . |
| 3,871,379 | 3/1975 | Clarke . |
| 4,018,229 | 4/1977 | Komiya . |
| 4,177,813 | 12/1979 | Miller et al. . |
| 4,923,461 | 5/1990 | Caspari . |
| 4,935,027 | 8/1990 | Yoon . |
| 5,100,415 | 3/1992 | Hayhurst . |
| 5,133,723 | 7/1992 | Li et al. . |
| 5,163,942 | 11/1992 | Rydell . |
| 5,176,691 | 1/1993 | Pierce . |
| 5,196,022 | 3/1993 | Bilweis . |
| 5,236,434 | 8/1993 | Callicrate . |
| 5,242,459 | 9/1993 | Buelna . |
| 5,281,238 | 1/1994 | Chin et al. . |
| 5,282,809 | 2/1994 | Kammerer et al. . |
| 5,290,284 | 3/1994 | Adair . |
| 5,300,078 | 4/1994 | Buelna . |
| 5,312,423 | 5/1994 | Rosenbluth et al. . |
| 5,318,578 | 6/1994 | Hasson . |
| 5,320,629 | 6/1994 | Noda et al. . |
| 5,330,491 | 7/1994 | Walker et al. . |
| 5,334,199 | 8/1994 | Yoon . |
| 5,336,231 | 8/1994 | Adair . |
| 5,383,882 | 1/1995 | Buess et al. . |
| 5,403,330 | 4/1995 | Tuason . |
| 5,403,331 | 4/1995 | Chesterfield et al. . |
| 5,423,837 | 6/1995 | Mericle et al. . |
| 5,445,167 | 8/1995 | Yoon et al. .................... 128/898 |

FOREIGN PATENT DOCUMENTS 0477020  3/1992  European Pat. Off. .

OTHER PUBLICATIONS

PortSaver PercLoop by Advanced Surgical, Inc. Features & Benefits and Specifications.

*Primary Examiner*—Michael Buiz
*Assistant Examiner*—Tina T. D. Pham

[57] ABSTRACT

A ligating instrument for forming ligatures in anatomical structure at an internal operative site in the body includes an elongate instrument body having a distal end for positioning at the operative site, a proximal end for positioning externally of the body and a lumen between the distal and proximal ends, a length of filamentous ligature material disposed in the lumen and forming a plurality of contractible ligature loops having knotting elements movable along the length of ligature material to contract the ligature loops and an operating member movable relative to the length of ligature material to move the knotting elements to contract the ligature loops. The ligature loops are withdrawable through the distal end of the instrument body for positioning around anatomical structure at the operative site. The operating member is movable, from externally of the body, to move the knotting elements to contract the ligature loops around the anatomical structure to form ligatures. A method of forming ligatures includes introducing the distal end of the instrument body at the operative site, withdrawing a ligature loop including the knotting element thereof through the distal end of the instrument body, positioning the withdrawn ligature loop around anatomical structure, and moving the operating member, from externally of the body, to move the knotting element of the withdrawn ligature loop to contract the ligature loop around the anatomical structure to form a ligature.

23 Claims, 9 Drawing Sheets

LIGATING INSTRUMENT WITH MULTIPLE LOOP LIGATURE SUPPLY AND METHODS THEREFOR

BACKGROUND OF THE INVENTION

1. Field of the Invention

The present invention pertains to ligating instruments and, more particularly, to ting instruments operable with one hand for use in endoscopic and non-endoscopic operative procedures and to methods therefor.

2. Discussion of the Prior Art

Closed or endoscopic operative procedures, also known as least-invasive procedures, have become extremely popular for use in many areas such as laparoscopy (pelviscopy), gastroentroscopy, laryngobronchoscopy and arthroscopy. In endoscopic operative procedures, access to an internal operative site in the body is gained through a relatively narrow or small size endoscopic portal establishing communication with the internal operative site from externally of the body. Accordingly, various instruments can be introduced at the operative site via the portal without the need for a skin incision of substantial size as is typically required for open procedures. Endoscopic procedures provide many benefits over open procedures including minimal invasiveness and trauma, fewer complications, shorter wound healing times, less patient discomfort, shorter hospitalization and rehabilitation times, cost savings and the ability to perform surgery without general anesthesia and in non-hospital or out-patient sites.

Ligating or tying anatomical tissue or organ structure is a time consuming and tedious part of both endoscopic and non-endoscopic operative procedures due to the difficulty involved in tying or applying an occluding ligature to anatomical structure as is desirable and/or necessary in many various procedures. Ligating anatomical structure is particularly difficult in endoscopic procedures due to the constraints on access to the operative site, the limited room for maneuverability at the operative site and the procedural or operational complexity required of many conventional endoscopic ligating instruments. Accordingly, the advantages of endoscopic procedures are sometimes outweighed by the disadvantages caused by the increased difficulty to ligate or tie and the increased length of time required to perform endoscopic procedures where such time is significantly extended due to the time required for ligation or tying.

Because endoscopic procedures are preferred over open procedures, much effort has been spent to develop instruments and techniques for facilitating tissue ligation. One technique involves the use of a ligating device, such as the Endoloop™ manufactured by Ethicon Endo-Surgery Inc. Various other ligating devices or instruments have been proposed, as exemplified by U.S. Pat. Nos. 5,383,882 to Buess et al, No. 5,336,231 to Adair, No. 5,334,199 to Yoon, No. 5,300,078 to Buelna, No. 5,290,284 to Adair, No. 5,281,238 to Chin et al, No. 5,242,459 to Buelna, No. 5,236,434 to Callicrate and No. 2,610,631 to Calicchio.

Many presently available ligating devices, instruments and procedures have various disadvantages including structural and operational complexity, tedious, difficult and time consuming procedural steps, the need for two-handed operation, the inability to sense or "feel" desired ligature tension and the inability to form multiple ligatures or ties without withdrawing the ligating devices or instruments from the body.

SUMMARY OF THE INVENTION

Accordingly, it is a primary object of the present invention to overcome the disadvantages of prior art ligating devices, instruments and procedures.

Another object of the present invention is to utilize a ligating instrument to form a plurality of ligatures at an internal operative site in the body without withdrawal of the ligating instrument from the body.

A further object of the present invention is to provide a ligating instrument including an elongate instrument body and a ligature supply including a plurality of preformed, contractible ligature loops of filamentous ligature material and having knotting elements movable along the ligature material in the direction of the ligature loops to contract the ligature loops around anatomical structure to form ligatures.

It is also an object of the present invention to provide a ligature supply including a plurality of interconnected ligature loops having knotting elements movable in a direction to contract the ligature loops around anatomical structure to form ligatures where the ligature loops including the knotting elements thereof are made of ligature material.

An additional object of the present invention is to move the distal end of the instrument body from a closed position preventing passage of the ligature loops therethrough to an open position permitting passage of the ligature loops therethrough to withdraw a ligature loop, including the knotting element thereof, from the instrument body for positioning around anatomical structure.

The present invention has as a further object to move the knotting elements, from externally of the body, with an operating member of the instrument body to reduce the size of the ligature loops distally to contract the externally positioned ligature loop around anatomical structure to form ligatures.

Yet another object of the present invention is to cut the ligature material proximally of a ligature to permit another ligature loop, including the knotting element thereof, to be withdrawn from the distal end of the instrument body to form another ligature without withdrawing the ligating instrument from the internal operative site in the body.

Some of the advantages of the present invention are that ligating anatomical structure is facilitated in both endoscopic and non-endoscopic procedures, the ligating instruments are operable with a single hand to form a plurality of ligatures, various diverse ligature supplies can be coupled with an instrument body allowing the optimal ligature supply to be selected in accordance with procedural use, ligatures can be formed in anatomical structure with a desired tension as tactilely sensed by the surgeon, cutting of the ligature material proximally of the ligatures can be accomplished with the same instrument or with a separate instrument depending on preferred procedural use, and the distal end of the ligating instrument can be utilized as a conductive element to treat tissue at the operative site.

These and other objects, advantages and benefits are realized with the present invention as generally characterized in a ligating instrument comprising an elongate instrument body and a ligature supply coupled with the instrument body. The instrument body includes a distal end for positioning at an internal operative site in the body, a proximal end for positioning externally of the body and a lumen between the distal and proximal ends. The distal end of the instrument body is movable, from externally of the body, from a closed position to an open position. The ligature supply includes a length of filamentous ligature material forming a plurality of interconnected, contractible ligature loops. Each ligature loop includes a knotting element movable along the length of ligature material to contract the ligature loops around anatomical structure to form ligatures. The ligature loops including the knotting elements thereof with the distal end in the closed position, are withdrawable from the instrument body through the distal end thereof when the distal end is in the open position to deploy the ligature loops at the operative site for positioning around anatomical structure. The knotting elements of the deployed ligature loops are prevented from passing through the distal end of the instrument body. The instrument body includes an operating member, operable from externally of the body, to move the knotting elements of the deployed ligature loops in the direction of the anatomical structure to contract the ligature loops around the anatomical structure to form ligatures.

A method of forming ligatures in anatomical structure according to the present invention includes the steps of introducing the distal end of the instrument body at the internal operative site, withdrawing a ligature loop including the knotting element thereof from the distal end of the instrument body to deploy the ligature loop at the operative site, positioning the deployed ligature loop around anatomical structure, moving the operating member, from externally of the body to move the knotting element of the deployed ligature loop relative to the length of ligature material to contract the ligature loop around the anatomical structure to form a ligature, and withdrawing another ligature loop from the distal end of the instrument body to form another ligature without withdrawing the ligating instrument from the body.

Other objects and advantages of the present invention will become apparent from the following description of the preferred embodiments taken in conjunction with the accompanying drawings, wherein like parts in each of the several figures are identified by the same reference characters.

DESCRIPTION OF THE PREFERRED EMBODIMENTS

Figure 1:
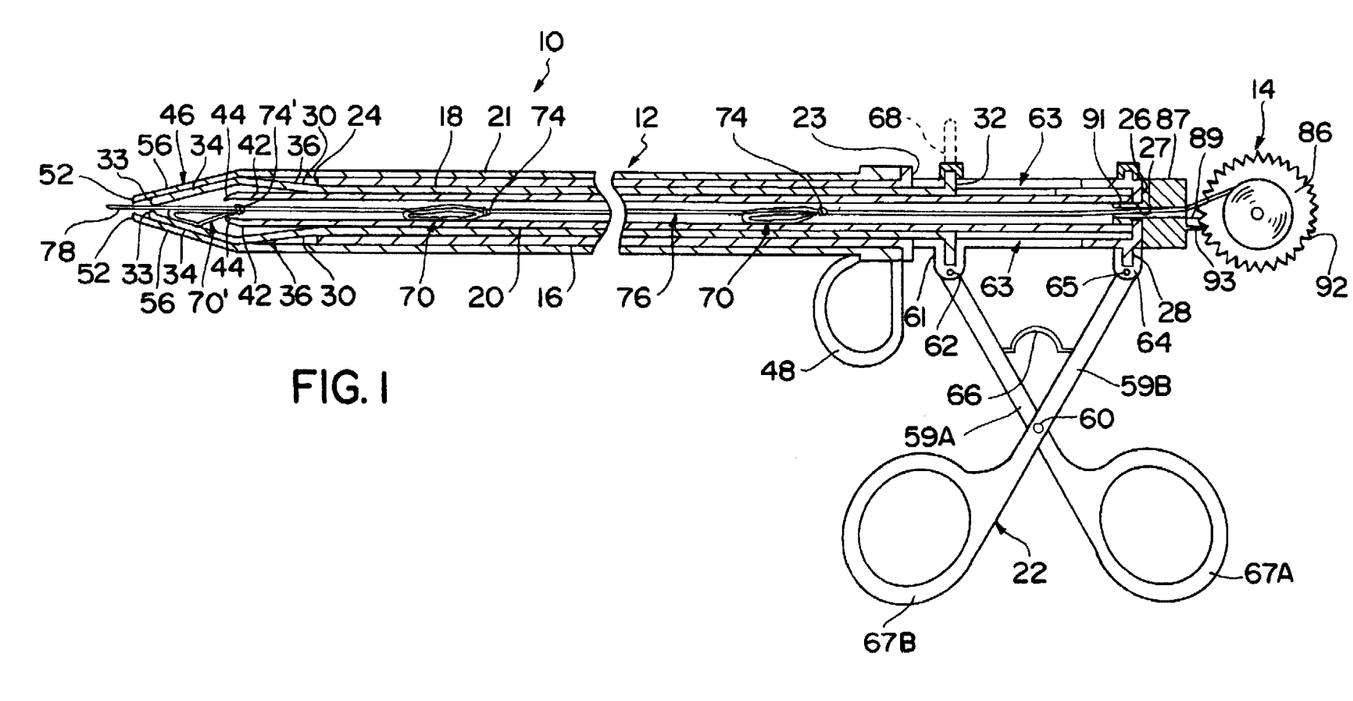
FIG. 1 is a broken side view, partly in section, of a ligating instrument according to the present invention.

A ligating instrument 10 according to the present invention is illustrated in FIG. 1 and includes an instrument body 12 and a multiple loop ligature supply 14 coupled with the instrument body. The instrument body 12 includes an elongate actuating member 16, an elongate jaw or forceps member 18 slidably disposed in actuating member 16, an elongate cutter 20 slidably disposed in jaw member 18, a knotting element pusher 21 disposed around actuating member 16 and a handle 22 mounting actuating member 16, jaw member 18 and cutter 20. With the exception of knotting element pusher 21, the instrument body 12 is similar to the instrument body disclosed in applicant's co-pending, prior application filed Sep. 5, 1995, and incorporated herein by reference. Actuating member 16 comprises a tubular or non-tubular hollow body terminating distally at an open distal end 24 and proximally at a proximal end including a transverse end wall 26. Actuating member 16 has a lumen between the distal and proximal ends communicating with a central aperture 27 in end wall 26. The proximal end of actuating member 16 is configured as or provided with a transverse or radially extending flange 28 coupled with handle 22 as explained further below.

The jaw member 18 comprises a tubular or non-tubular hollow body and a pair of opposed jaws 30 extending distally from the jaw member body, the jaws 30 being modified slightly from the jaws disclosed in the aforementioned prior application filed Sep. 15, 1995, and incorporated herein by reference. The jaw member body preferably has an external diameter or cross-sectional size to be closely received within actuating member 16 while allowing actuating member 16 and jaw member 18 to be moved longitudinally relative to one another. The jaw member body terminates proximally at an open proximal end configured as or provided with a transverse or radially extending flange 32 coupled with handle 22 as explained further below. Each jaw 30 includes a forward section 34 and a rearward section 36. Each forward section 34 terminates distally at a tip 33 and proximally at the corresponding rearward section 36 with the forward sections being angled inwardly from the corresponding rearward sections in the direction of a longitudinal axis of the jaw member. Each rearward section 36 extends proximally and angularly inwardly from the corresponding forward section 34 in the direction of the jaw member longitudinal axis to merge with the jaw member body. The walls defining the forward and rearward sections are of uniform or substantially uniform thickness to define a hollow interior for the jaws communicating with the lumen or hollow interior of the jaw member body. Jaws 30 are normally disposed in an open position wherein jaw tips 33 are separated from one another by a variable size distance defining a space, opening or passage communicating with the hollow interior of the jaws. Jaws 30 are movable inwardly toward one another, i.e. toward the longitudinal axis of the jaw member, from the normally open position to a closed position by engagement of the distal end 24 of actuating member 16 with the walls forming rearward sections 36 as shown in FIG. 1. In the closed position, jaw tips 33 are disposed closer to one another and, therefore, closer to the jaw member longitudinal axis, than they are in the open position such that the distance between the jaw tips 33 is less than the distance between the jaw tips in the open position. The distance between jaw tips 33 in the closed position is small enough to prevent passage therethrough of the ligature loops of ligature supply 14, and the distance between jaw tips 33 in the open position is large enough to permit passage therethrough of the ligature loops as explained below. Jaws 30 are maintained in the closed position due to constraint by actuating member 16; and, when actuating member 16 is moved proximally relative to the jaw member 18 and/or the jaw member 18 is moved distally relative to the actuating member 16, the jaws 30 automatically move toward the open position. The jaws can be designed in many various ways to be normally disposed in the open position and to be moved to and maintained in the closed position or the jaw member can be normally disposed in the closed position and moved to an open position. In the case of instrument 10, the jaws 30 are made of resilient, flexibly, spring materials to be flexible and/or spring or resiliently biased in the open position.

The cutter 20 comprises a tubular or non-tubular hollow body having a proximal end connected to end wall 26, a distal end carrying or formed as opposed, longitudinally extending cutting fingers 42 and a lumen, internal passage or channel aligned with aperture 27. The cutter 20 preferably has an external diameter or cross-sectional size to be closely received within the jaw member 18 while allowing the jaw member and cutter to move longitudinally relative to one another. The cutting fingers 42 carry or are formed as inwardly curving or angled cutting blades 44 and are normally disposed in a non-cutting position wherein the cutting blades 44 are separated or spaced from one another by a distance defining a space or passage between the cutting blades 44 allowing ligature material of the ligature supply 14 to pass between the cutting blades 44 as shown in FIG. 1. The cutting fingers 42 are movable inwardly toward one another in the direction of a longitudinal axis of cutter 20 from the non-cutting position to a cutting position wherein the cutting blades 44 are disposed closer to one another to cut the ligature material therebetween. The distance between the cutting blades 44 in the non-cutting position is sufficiently large to allow passage of the ligature loops between the blades 44 without damage when the cutter is in the non-cutting position. The cutting fingers or blades can be designed in many various ways to be normally disposed in the non-cutting position and to be moved to the cutting position. In the case of instrument 10, the cutting fingers 42 are made of resilient, flexible or spring materials to be flexibly, resiliently and/or spring biased in the non-cutting position and to be moved to the cutting position by engagement of the cutting fingers with the inner surfaces of the walls forming the angled forward sections 34 of jaws 30 as explained further below. Various cutters suitable for use in the ligating instruments according to the present invention are disclosed in applicant's prior applications Ser. No. 08/195,491, filed Feb. 14, 1994, and Ser. No. 07/930,320, filed Aug. 17, 1992, and now U.S. Pat. No. 5,334,199, the disclosures of which are incorporated herein by reference.

Figure 2:
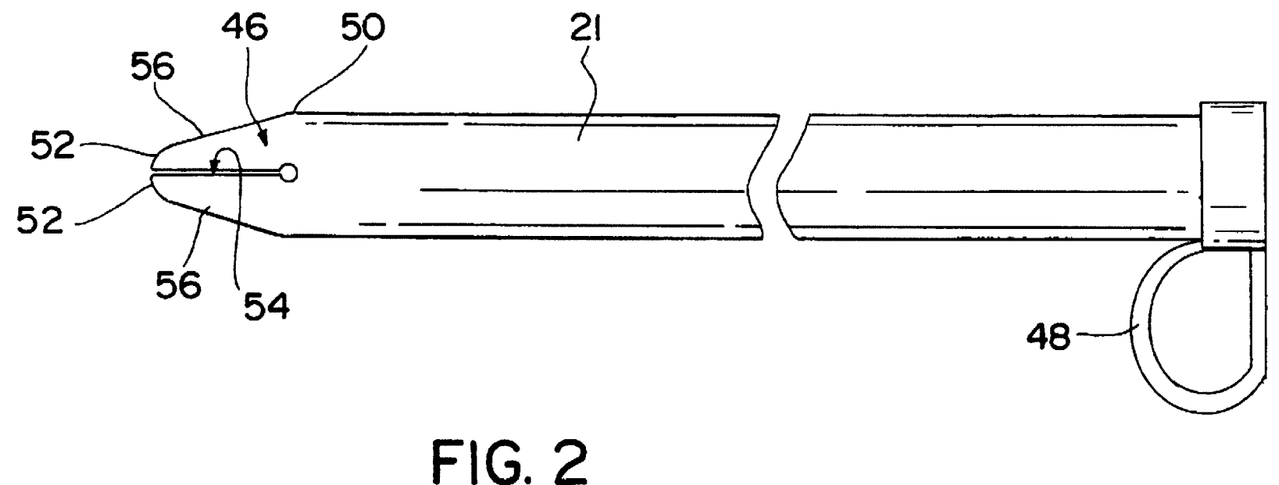
FIG. 2 is a broken side view of the knotting element pusher of the ligating instrument of FIG. 1 showing the pusher end in a closed position.

Knotting element pusher 21, as shown in FIG. 2, comprises an elongate tubular or hollow body and a pusher end 46 extending distally from the pusher body. The pusher body terminates proximally at an open proximal end configured as or provided with a depending finger ring 48 for being manually engaged by a hand grasping handle 22 as explained further below. The pusher body terminates distally at a junction 50 joining the pusher body to the pusher end 46. The pusher body preferably has an external diameter or cross-sectional size sufficiently small to be introduced at an internal operative site in the body through a relatively small size or narrow endoscopic portal for use in endoscopic procedures wherein the endoscopic portal establishes communication with the internal operative site from externally of the body. The pusher body preferably has an internal diameter or size to be frictionally held by actuating member 16 while being movable along and relative to actuating member 16 via a manual force, sufficient to overcome the frictional force, applied with finger ring 48 as explained below. Pusher end 46 is hollow and tapers distally from junction 50 to a pusher tip. A slit or cut 54 extends entirely through pusher end 46 from tip 52 to junction 50 in a plane containing a longitudinal axis of pusher 21. Slit 54, which terminates at rounded edges at junction 50, divides pusher end 46 into opposed push fingers 56 having distal tips 52, respectively. It should be appreciated, however, that the pusher end can be designed in various ways to include any desired number of push fingers. As shown in FIG. 2, pusher end 46 is normally disposed in a closed position wherein pusher tips 52 are disposed close to one another and to the pusher longitudinal axis while being separated slightly from one another by a distance preventing passage of the ligature loops of the ligature supply 14 between the pusher tips 52. Pusher end 46 is movable to an open position wherein push fingers 56 are spread outwardly in a direction away from the pusher longitudinal axis and pusher tips 52 are disposed further away from one another and from the pusher longitudinal axis to be separated from one another by a greater distance allowing the ligature loops to pass therebetween. The pusher end can be designed in many ways to be normally disposed in the closed position and to be movable to the open position. In the case of pusher 21, push fingers 56 are made of resilient, flexible or spring materials to be resiliently, flexibly or spring biased in the closed position and the opening bias or force of jaws 30 is greater than the closing bias or force of the push fingers 56 such that the pusher end 46 is opened or spread by jaws 30 as explained further below. It should be appreciated that the pusher end does not have to be normally disposed in the closed position; rather, the pusher end can be normally disposed in an open position and moved to a closed position during operation of the ligating instrument. An external or outer surface of pusher 21 can have a scale thereon including indicia for taking measurements in the body as disclosed in applicant's aforementioned copending prior application file Sep. 15, 1995, and incorporated herein by reference.

Handle 22 includes a pair of hand grips 59A and 59B pivotally connected to one another at a joint 60 including a pin passing through the hand grips. An upper end of hand grip 59A is pivotally connected to a retention block 61 having a recess therein for receiving flange 32 of jaw member 18, the hand grip 59A being connected to the retention block 61 at a joint 62 including a pin passing through the retention block and the hand grip. Longitudinal slots 63 are formed in actuating member 16, and the jaw member flange 32 passes through and is movable along the slots 63. Actuating member 16 has a flange or abutment 23 at a distal end of slots 63 serving as a positive stop limiting proximal movement of pusher 21 to position pusher 21 during use as described further below. An upper end of hand grip 59B is pivotally connected to a retention block 64 having a recess therein for receiving flange 28 of actuating member 16, the hand grip 59B being connected to the retention block 64 at a joint 65 including a pin passing through the retention block 64 and the hand grip 59B. A curved spring 66 is connected between the upper ends of hand grips 59A and 59B and maintains the handle 22 in a rest position as shown in FIG. 1 wherein the upper ends of the hand grips 59A and 59B are spaced from one another. Lower ends of hand grips 59A and 59B are configured as circular or substantially circular finger rings 67A and 67B, respectively, by means of which the handle may be grasped to manipulate and operate the instrument. Handle 22 can be manually squeezed or compressed via finger rings 67A and 67B causing the upper ends of hand grips 59A and 59B to be moved from the rest position toward one another, or the handle 22 can be manually spread causing the upper ends of hand grips 59A and 59B to be moved from the rest position further away from one another. In each case, removal of the manual force results in the handle being returned to the rest position by the restoring force of spring 66. An insulated connector can be connected with an electrically conductive element of the instrument 10 for performing unipolar or bipolar electric coagulation. For example, a connector 68, shown in dotted lines in FIG. 1, enters retention block 61 at upper longitudinal slot 63 and is connected with the jaw member 18, which is made of electrically conductive material allowing jaws 30 to be used as conductive elements.

Figure 3:
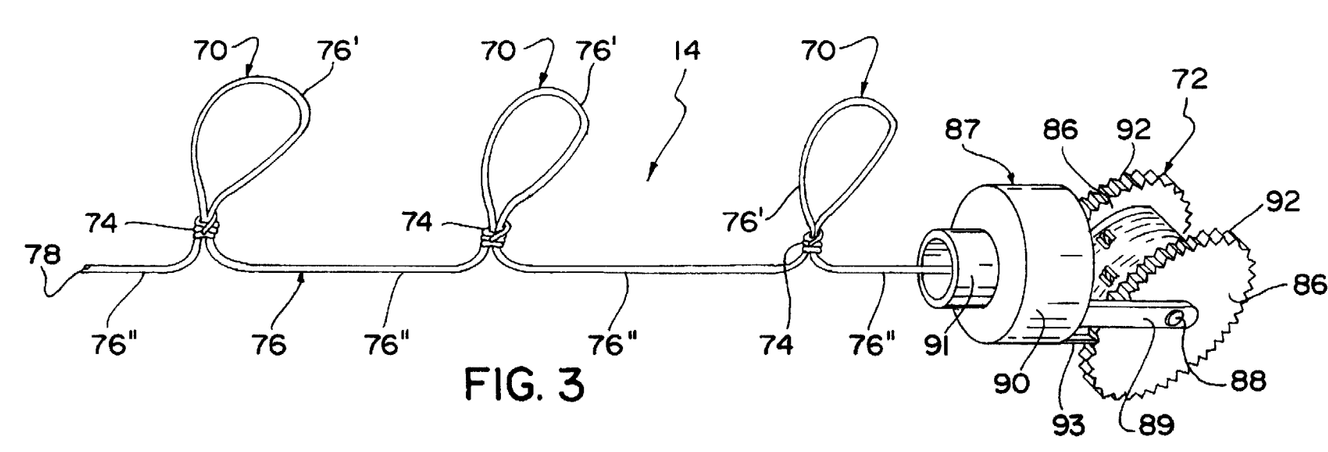
FIG. 3 is a broken perspective view of the ligature supply of the ligating instrument of FIG. 1.

As shown in FIG. 3, ligature supply 14 comprises a plurality of serially arranged, pre-formed, variable size or contractible ligature loops 70 of filamentous ligature material connected to one another and carried by or wound on a spool or wheel 72. Each ligature loop 70 includes a movable knotting element 74 movable along the ligature material to contract or reduce the size of the ligature loop around anatomical structure to form a ligature. Movable knotting elements 74 are in the nature of knots formed in a length of single filament ligature material 76 from which ligature loops 70 are also formed. Accordingly, each ligature loop 70 is defined by a knot 74 and a continuous loop segment 76' of the length of ligature material extending from the knot 74 and back to the knot 74. Knots 74 have a size to prevent passage of the ligature loops between the jaw tips 33 with the jaws 30 in the closed position while permitting passage of the ligature loops between the jaw tips 33 when the jaws 30 are in the open position. The size of knots 74 prevents passage of the ligature loops between pusher tips 52 when the pusher end 46 is in the closed position and permits passage of the ligature loops between the pusher tips 52 when the pusher end 46 is in the open position. In the case of ligature supply 14, knots 74 are sufficiently large to prevent passage of the knots between the jaw tips 33 and the pusher tips 52 in the closed position. Ligature material 76 comprises a filament having an external diameter or size permitting passage of the filament between jaw tips 33 when the jaws 30 are in the closed position and between pusher tips 52 when the pusher end 46 is in the closed position. Ligature loops 70 are disposed at spaced locations along the length of ligature material such that connecting segments 76" of the length of ligature material extend between adjacent ligature loops 70. As shown in FIG. 3, a connecting segment 76" extends distally from the knot of the middle ligature loop to the knot of the forward ligature loop, and a connecting segment 76" extends proximally from the knot of the middle ligature loop to the knot of the rearward ligature loop. A connecting segment 76" extends distally from the knot of the forward ligature loop to a next forward ligature loop (not shown) or to form a free end or tail 78 as shown in FIGS. 1 and 3. A connecting segment 76" extends proximally from the knot of the rearward ligature loop to a next rearward ligature loop or to form an end for being connected to or wound around spool 72.

Figure 4:
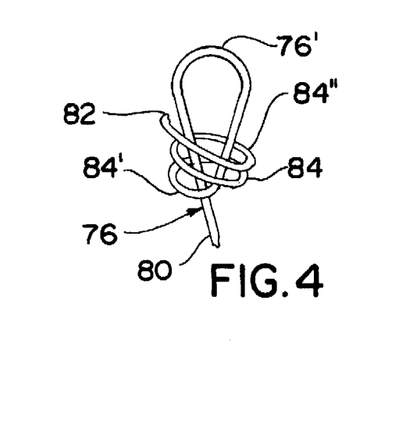
FIG. 4 is a broken perspective view illustrating a first step in forming a ligature loop and movable knotting element of the ligature supply of FIG. 3.
Figure 5:
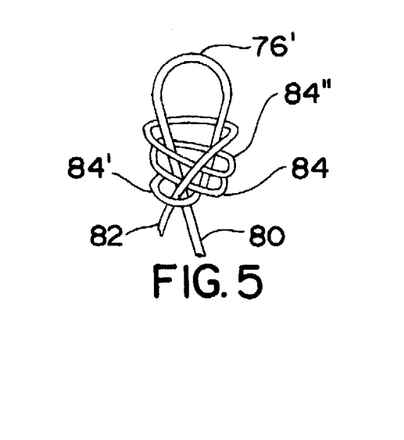
FIG. 5 is a broken perspective view illustrating a second step in forming the ligature loop and movable knotting element.
Figure 6:
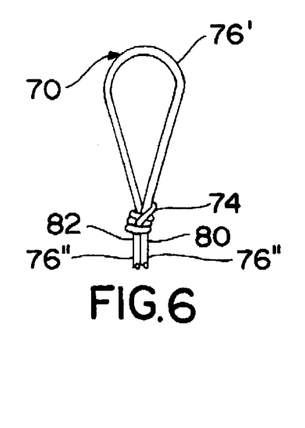
FIG. 6 is a broken perspective view illustrating a third step in forming the ligature loop and movable knotting element.

Knots 74 can be in the nature of slip, sliding or hangman's knots, for example, or any other type of knot permitting movement of the knot along the length of ligature material in the direction of the corresponding ligature loop to reduce the size of the corresponding ligature loop. FIGS. 4–6 illustrate one manner of forming a ligature loop 70 and a knot 74 for ligature supply 14. As shown in FIG. 4, the length of ligature material 76 is folded or arranged to form loop segment 76' having ends 80 and 82. End 82 is wrapped around a lower portion or base of loop segment 76' several times, preferably two or three times, to form a plurality of adjacent loops 84 around the base of loop segment 76', the loops 84 being formed with end 82 from a lowermost loop 84' to an uppermost loop 84". End 82 is positioned to extend externally over the uppermost loop 84" and the upper loop 84 and is inserted through the top of the lowermost loop 84' as shown in FIG. 5. Loops 84 are made taut thusly forming knot 74 at the base of loop segment 76' with ends 80 and 82 extending from knot 74 to form the connecting segments 76" as shown in FIG. 6. Knot 74 defines a proximal end of the corresponding ligature loop 70 and is movable distally or forwardly along end 80 in the direction of the corresponding ligature loop 70 to contract the ligature loop 70 while end 80 is held in place. It should be appreciated that various other types of movable knotting elements capable of being moved along the ligature material to contract the ligature loops, including separate knotting elements not formed from the length of ligature material, can be utilized in the present invention. It should be further appreciated that the movable knotting elements can also be designed to prevent expansion of the ligature loops once the ligature loops have been contracted or reduced in size. Various knotting elements suitable for use in the present invention are disclosed in applicant's prior application filed Sep. 15, 1995, and in applications Ser. No. 08/366,285, Ser. No. 08/377,723 and Ser. No. 08/401,002 incorporated herein by reference.

As shown in FIG. 3, spool 72 includes a pair of circular end flanges 86 connected by a cylindrical shaft around which the length of ligature material 76 carrying ligature loops 70 and knotting elements 74 is wound. Spool 72 is removably coupled to an adapter 87 via a removable pin 88 passing through a pair of mounting bars 89 extending proximally from a cylindrical body 90 of adapter 87. Adapter 87 includes cylindrical body 90 and a tubular extension 91 extending distally from a distal shoulder of cylindrical body 90. Cylindrical body 90 has an internal bore or passage aligned with the lumen of tubular extension 91 allowing the length of ligature material to extend entirely through the adapter when the spool 72 is mounted thereto. Tubular extension 91 has an external diameter to be frictionally received in the lumen of cutter 20 and/or aperture 27 to couple the ligature supply with the instrument body. The spool 72 can be mounted to various adapters having different size tubular extensions for coupling to various size instrument bodies. The adapter can be removably coupled with the instrument body in various ways including the use of a friction fit or threaded connection, for example. The mounting bars 89 can be made flexible to flex outwardly from one another to facilitate mounting, removal and/or replacement of spool 72 on adapter 87. The spool 72 can be mounted on adapter 87 in various ways and the adapter 87 can be mounted to the instrument body in various ways to position the spool for rotation or operation by the hand grasping handle 22.

A plurality of teeth 92 are formed along the circumference of end flanges 86 for cooperating with pawls 93 extending proximally from a rearward shoulder of cylindrical body 90 to form a rotational control mechanism for controlling rotation of spool 72. As shown in FIGS. 1 and 3, wherein one pawl 93 is shown for one end flange 86, each pawl 93 includes a flexible or resilient strip or tab having a first end secured to adapter body 90 and a second end positioned between two adjacent teeth 92 to prevent rotation of spool 72. Pawl 93 is bendable, flexible or pivotable about the first end thereof to disengage the second end from teeth 92 when the spool 72 is manually rotated with sufficient force in either a clockwise or counterclockwise direction. For example, counterclockwise rotation of spool 72, looking at FIGS. 1 and 3, will cause pawl 93 to be bent or flexed downwardly causing the second end thereof to be disengaged from teeth 92 to permit counterclockwise rotation of spool 72 when spool 72 is rotated with a manual force sufficient to overcome the holding force of pawl 93. Once the spool 72 has been rotated a desired increment, pawl 93 will spring back into engagement with teeth 92 to maintain the position of the spool 72.

The instrument body 12 will normally be supplied as shown in FIG. 1 with the jaw member 18 concentrically disposed in actuating member 16, cutter 20 concentrically disposed in jaw member 18 and pusher 21 disposed over actuating member 16. Handle 22 will be in the rest position to position actuating member 16, jaw member 18 and cutter 20 such that jaws 30 protrude distally from actuating member 16 and are maintained by actuating member 16 in the closed position due to engagement of the actuating member distal end 24 with the walls defining the rearward sections 36 of the jaws. Cutting fingers 42 will be disposed in the hollow interior of the jaws in the non-cutting position with cutting blades 44 positioned proximally of the angled inner surfaces of the walls defining forward sections 34. The proximal end of pusher 21 will be in abutment with the flange 23 of actuating member 16, and the pusher end 46 will be in the closed position with pusher tips 52 disposed distally of jaw tips 33 with the jaws 30 received within the hollow interior of the pusher end.

Figure 7:
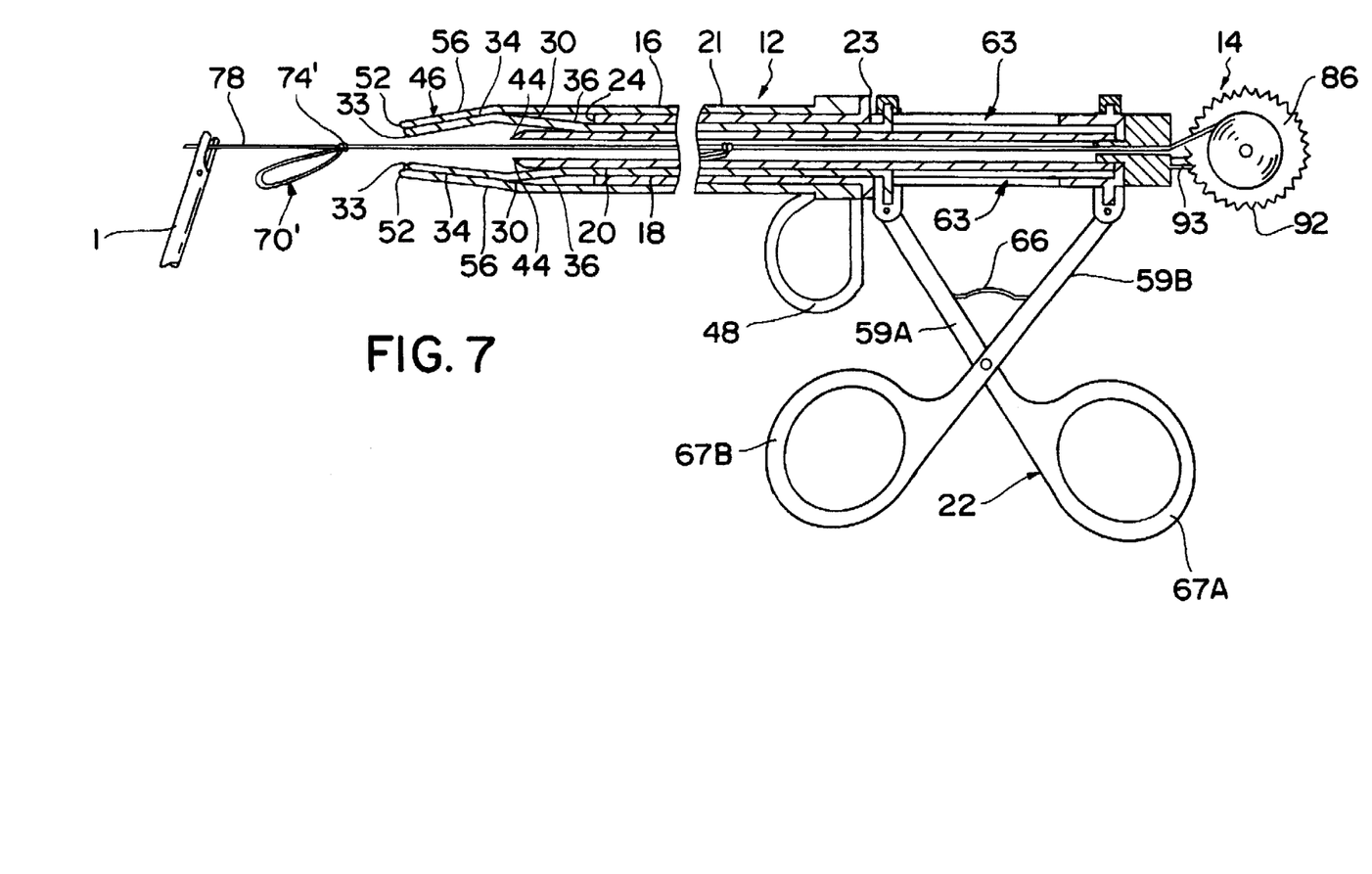
FIG. 7 is a broken side view, partly in section, of the ligating instrument of FIG. 1 showing deployment of the first ligature loop.

Ligating instrument 10 can be supplied assembled, with tubular extension 92 held in the lumen of cutter 20 and/or aperture 27 to couple the ligature supply 14 with the instrument body 12 as shown in FIG. 1. Where the ligating instrument 10 is supplied assembled, the length of ligature material 76 will be partially unwound from spool 72 to extend through adapter 87 and into the instrument body. The length of ligature material 76 will extend through cutter 20 and between the jaw tips 33 and the pusher tips 52 such that tail 78 protrudes externally of the pusher tips 52 while the first ligature loop 70' remains within the instrument body. It should be appreciated that the instrument can be supplied for use with no parts of the ligature material protruding distally from the instrument body. Where the instrument is supplied for use with part of the ligature material protruding distally therefrom, the protruding part can include, for example, tail 78, the first ligature loop 70' and/or the first knotting element 74'. Instrument 10 can be supplied unassembled with the ligature supply 14 not coupled with the instrument body 12. A particular ligature supply can optimally be selected in accordance with procedural use, and the length of ligature material 76 of the selected ligature supply is fed through aperture 27. The tubular extension 91 of the ligature supply is inserted into the instrument body via aperture 27. Where a part of the ligature material does not already protrude from the distal end of the instrument body and it is desired to position part of the ligature material externally of the distal end of the instrument body prior to introduction at the operative site, handle 22 is spread via finger rings 67A and 67B to move the jaw member 18 distally and/or the actuating member 16 proximally relative to one another as permitted by slots 63. In the case of instrument 10, actuating member 16 and cutter 20 move slightly proximally and jaw member 18 moves slightly distally in response to spreading operation of handle 22 causing jaws 30 to move to the open position due to release of the jaw rearward sections 36 from constraint by the distal end 24 of actuating member 16 as shown in FIG. 7. Pusher 21 and cutter 20 move with actuating member 16, and the pusher end 46 is moved to the open position due to spreading of the push fingers 56 by the jaws 30. With jaws 30 and pusher end 46 in the open position, the ligature material 76 can be grasped, such as by grasping tail 78 and/or another part of the ligature material with a grasper or forceps instrument. The grasper, which can be inserted between the open jaws and push fingers is used to pull or move the ligature material distally between the jaw tips 33 and pusher tips 52 until a desired part or portion of the ligature material protrudes externally of the pusher tips 52. The ligature material is pulled with a force sufficient to overcome the force of pawl members 93 permitting counterclockwise rotation of spool 72 and, therefore, unwinding of the ligature material or the spool 72 is manually rotated counterclockwise to unwind the ligature material therefrom prior to or simultaneously with the ligature material being pulled. Upon release of handle 22 from the spread position, the handle will be returned to the rest position by spring 66, the jaws 30 will be moved to the closed position due to constraint by actuating member 16 and the pusher 21 will be returned to the position shown in FIG. 1 with pusher end 46 in the closed position.

In use, a distal end of the ligating instrument 10 is introduced at an internal operative site with the instrument body in the position shown in FIG. 1 with jaws 30 and pusher end 46 in the closed position and with part of the ligature material, such as tail 78, protruding from pusher tips 52 or with no parts of the ligature material protruding from the pusher tips. In endoscopic procedures, the ligating instrument is introduced at the operative site through an endoscopic portal including a structural sleeve or channel such as a portal or trocar sleeve or a small size natural or prepared anatomical opening establishing communication with the internal operative site from externally of the body. Handle 22, which is held with one hand externally of the body, is used to manipulate the ligating instrument to position the distal end thereof within the body, the pusher tips 52 defining a distal end for the instrument body 12. To deploy the first ligature loop 70' handle 22 is spread to open jaws 30 and pusher end 46 as described above and as shown in FIG. 7. Accordingly, the actuating member 16, cutter 20 and pusher 21 will all move slightly proximally and the jaw member 18 will move slightly distally. The jaws 30 will be moved to the open position due to release of the jaw rearward sections 36 from constraint by the actuating member distal end 24. The stronger opening force of jaws 30 will overcome the closing force of pusher end 46 causing push fingers 56 to be spread. The cutter 20, which moves proximally with the actuating member 16, will remain in the non-cutting position. Both the jaws 30 and the pusher end 46 will be in the open position allowing the ligature loops to pass between the jaw tips 33 and the pusher tips 52. The ligature material 76 is pulled distally, such as with a grasper I introduced through a second endoscopic portal, until the first ligature loop 70' including the first knotting element 74' thereof is withdrawn from the instrument body and is disposed externally of the pusher tips 52 as shown in FIG. 7. Once the first ligature loop 70' is disposed externally of the pusher tips 52 as permitted by movement of the first ligature loop 70' including its knotting element 74' between the jaw tips 33 and the pusher tips 52 when the jaws 30 and the pusher end 46 are in the open position, handle 22 is moved to the rest position causing the jaws to move to the closed position. The first ligature loop 70' will be held externally of the pusher 21 since the first movable knotting element 74' cannot enter or pass proximally between the pusher tips 52 once the pusher end 46 is in the closed position as shown in FIG. 8.

Figure 8:
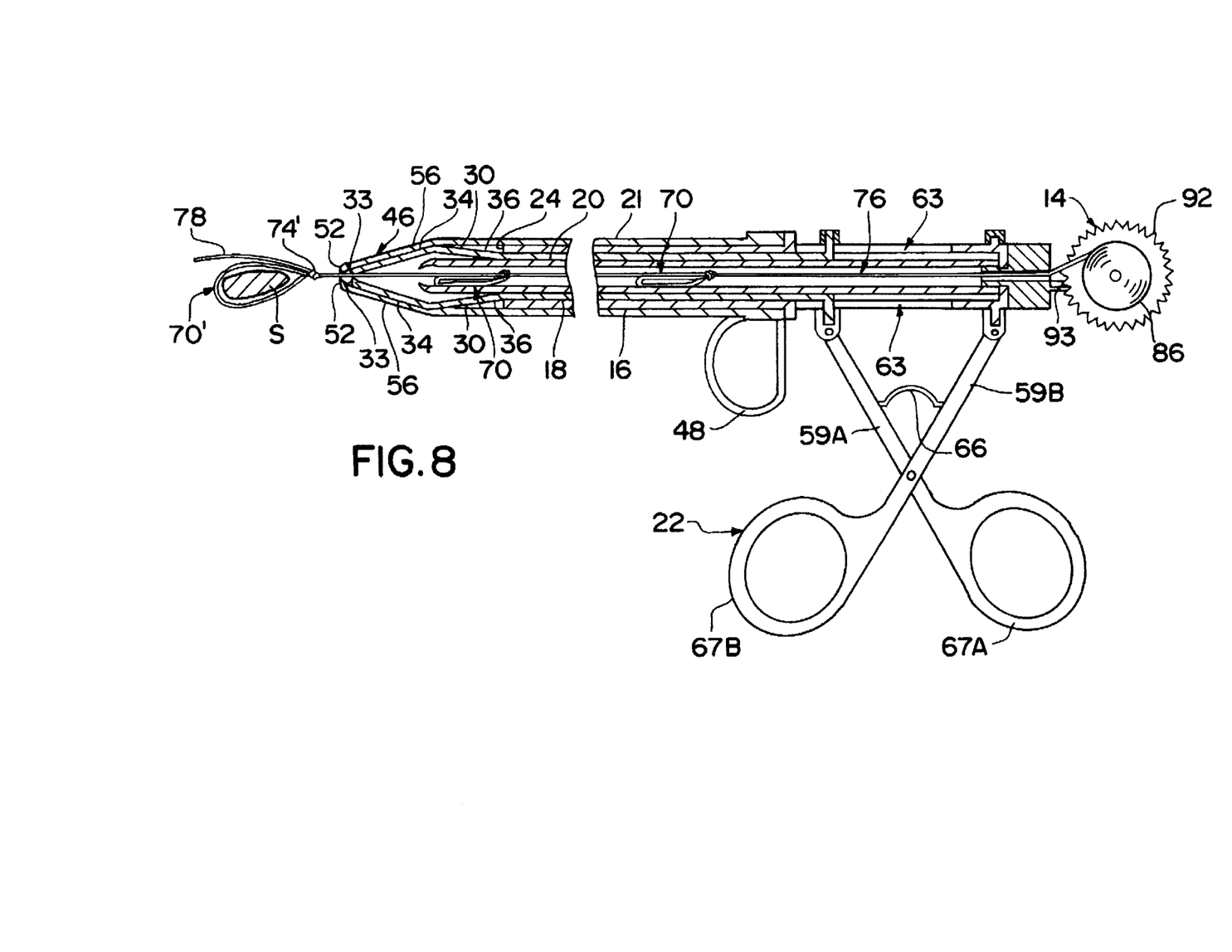
FIG. 8 is a broken side view, partly in section, of the ligating instrument showing the first ligature loop positioned around an anatomical structure.
Figure 9:
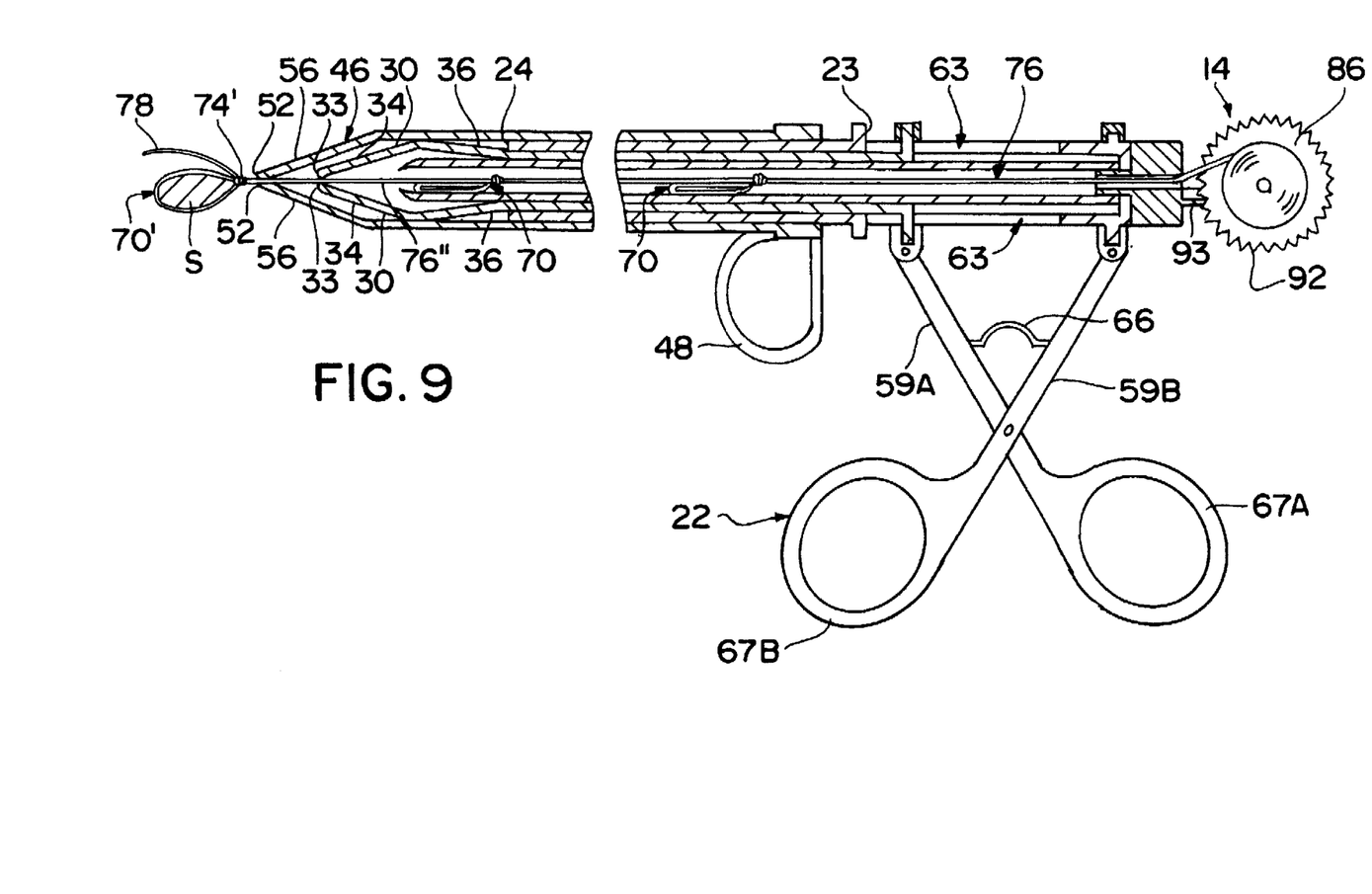
FIG. 9 is a broken side view, partly in section, of the ligating instrument showing the first ligature loop contracted around the anatomical structure to form a ligature.

To utilize the ligating instrument 10 to form a ligature in anatomical structure including anatomical tissue structure, anatomical organ structure or any other anatomical part which it is desirable or necessary to ligate, tie or occlude, the distal end of the instrument 10 is positioned adjacent the anatomical structure S to be ligated, and the external ligature loop 70' is positioned around the anatomical structure S as shown in FIG. 8. Once the ligature loop 70' has been positioned around the anatomical structure S, the finger ring 48 is engaged by a finger of the hand grasping handle 22 and is manually moved distally with a force sufficient to overcome the frictional holding force of the pusher 21 on the actuating member 16. The pusher 21 is moved distally relative to actuating member 16 and, therefore, the length of ligature material 76 extending through the instrument body, so that the pusher tips 52 engage the knotting element 74'. The knotting element 74' will be prevented from moving between the pusher tips 52 since the push fingers 56 are in the closed position. The pusher 21 is moved distally, i.e. toward the anatomical structure S, relative to the ligature material 76 to push knotting element 74' distally along the connecting segment element 76" to contract or reduce the size of loop 70' around anatomical structure S to form a ligature as shown in FIG. 9. The spool 72 can be manually rotated clockwise to ensure that the ligature material extending through the instrument body is taut to facilitate movement of the knot.

Figure 10:
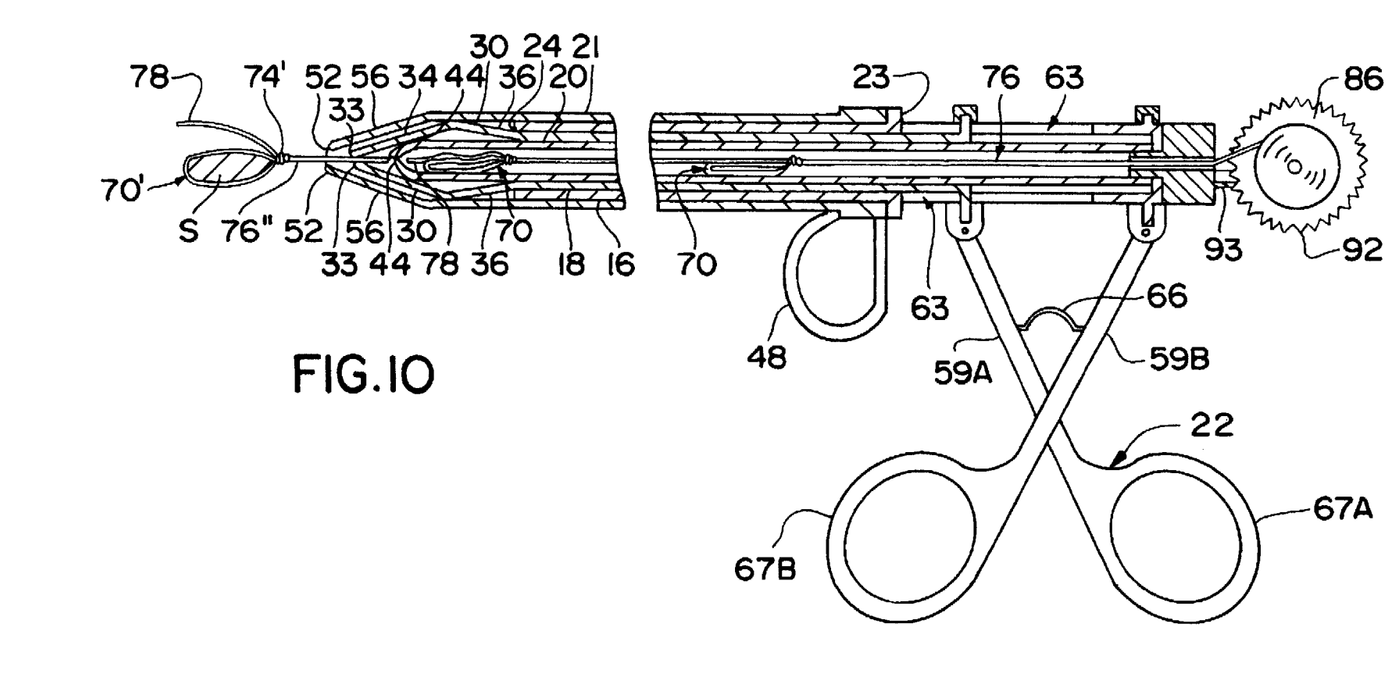
FIG. 10 is a broken side view, partly in section, of the ligating instrument showing the ligature material being cut proximally of the ligature.

Once the ligature loop 70' has been tightened or contracted around the anatomical structure S with a desired tension, which can be tactilely sensed or felt by the surgeon via the finger ring 48, the pusher 21 is moved proximally until the pusher proximal end is again in abutment with flange 23. Handle 22 is squeezed causing actuating member 16 and/or jaw member 18 to move relative to one another to move jaws 30 to a second or further closed position. In instrument 10, actuating member 16 is moved slightly distally and jaw member 18 is moved slightly proximally when handle 22 is squeezed causing the distal end 24 of actuating member 16 to push inwardly on the walls forming jaw rearward sections 36. Accordingly, jaws 30 are moved inwardly in the direction of a longitudinal axis of the instrument to a further or second closed position and cutter 20 is moved distally with actuating member 16 to engage the angled inner surfaces of the walls defining forward sections 34 to move the cutter to the cutting position wherein cutting blades 44 are moved inwardly to cut the length of ligature material 76 proximally of the ligature as shown in FIG. 10. Pusher 21 moves distally with actuating member 16 and cutter 20 and remains in the closed position. If desired, tail 78 can be trimmed with a separate cutting instrument.

After the length of ligature material 76 has been cut proximally of the knotting element 74', the ligature is left in place and the instrument 10 can be utilized to form another ligature. The handle 22 is spread to open jaws 30 and push fingers 56 allowing the next ligature loop to be withdrawn from the instrument body and positioned externally of the pusher tips 52. For example, a grasper or forceps I can be utilized to grasp the new free end or tail 78 of the length of ligature material, and the spool 72 can be rotated counter-clockwise to unwind the length of ligature material for advancement through the instrument body. It should be appreciated that the instrument can be designed with a mechanism for driving or pushing the ligature material through the instrument body. For example, the instrument body can include friction rollers or a control trigger which causes a pusher to advance a ligature loop externally of the jaws. Accordingly, the ligating instrument 10 will be ready for use to form another ligature or tie without withdrawal of the instrument from the body.

It should be appreciated that use of the ligating instrument can include contacting anatomical tissue or structure with the jaws and transmitting electrical energy to the tissue to treat the tissue, such as for electrical coagulation, via the jaws and connector 68. In the latter case, the instrument body 12 can be provided without stop 23 allowing the pusher 21 to be manually moved proximally from the position shown in FIG. 1 relative to jaw member 18. Movement of pusher 21 proximally relative to jaw member 18 causes the pusher end 46 to be moved to the open position due to spreading of the push fingers 56 by the jaws 30. Accordingly, the push fingers 56 will be moved proximally relative to the jaws 30 such that the jaws 30 will protrude distally beyond the push fingers and will be exposed for use as conductive elements. In addition, use of the ligating instrument can include taking measurements or dimensions in the body via the scale on pusher 21, such as taking measurements of organs, tissue or other anatomical structure as well as tumors and anatomical voids, cavities and spaces.

Figure 11:
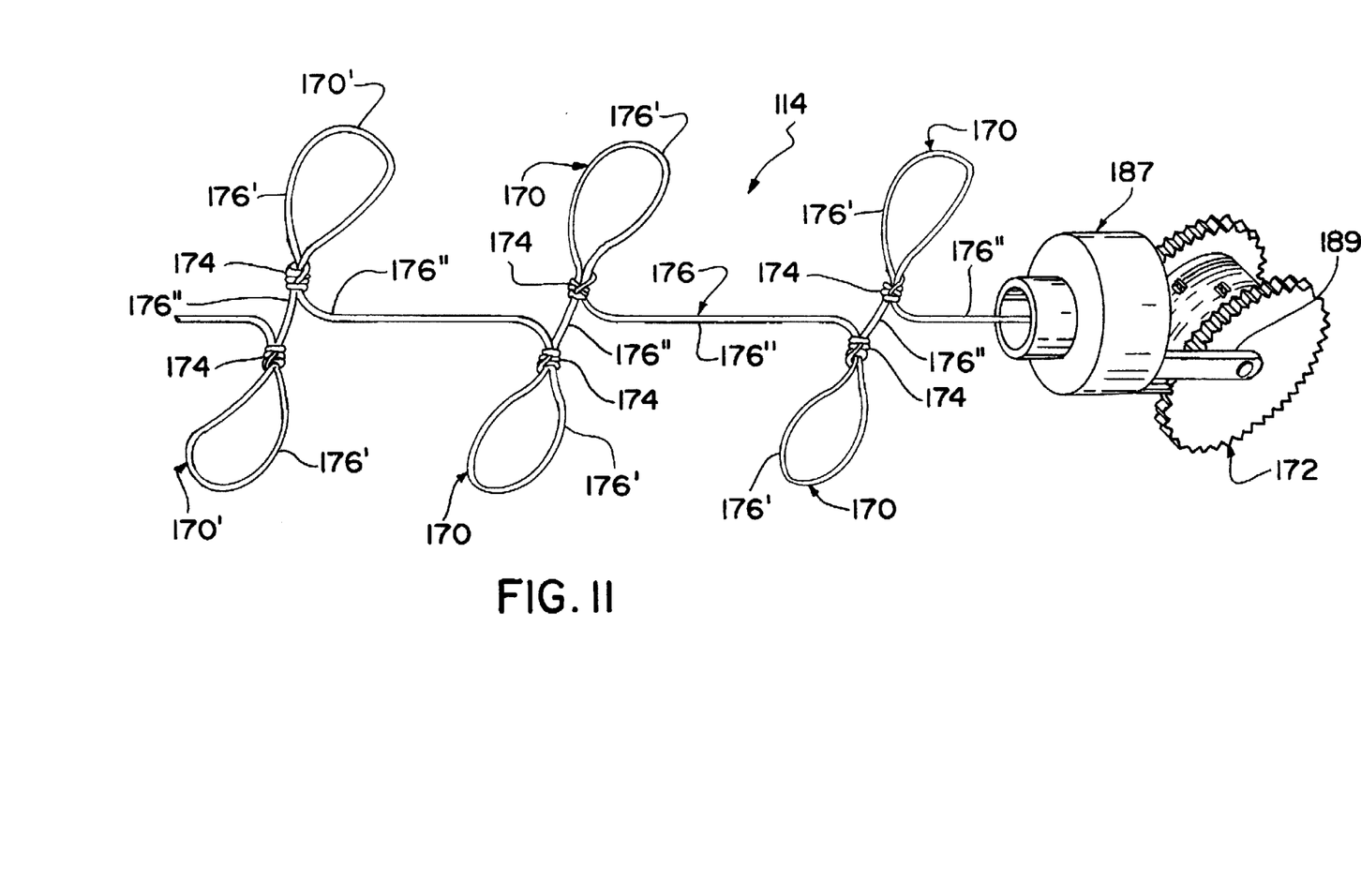
FIG. 11 is a broken perspective view of a modification of a ligature supply according to the present invention.

A modification of a ligature supply according to the present invention is illustrated at 114 in FIG. 11. Ligature supply 114 is similar to ligature supply 14 and includes ligature loops 170 each formed by a loop segment 176' and a knot 174 formed in a length of single filament ligature material 176. Ligature supply 114 differs from ligature supply 14 in that ligature loops 170 are formed along the length of ligature material 176 to be arranged in spaced pairs. As shown in FIG. 11, a forward pair of bilaterally arranged ligature loops 170 are disposed relatively close to or adjacent one another and are spaced from a middle pair of bilaterally arranged ligature loops which are also disposed relatively close to or adjacent one another. The middle pair of ligature loops are in turn spaced from a rearward pair of bilaterally arranged ligature loops disposed relatively close to or adjacent one another. Accordingly, the connecting segments 176" of the length of ligature material extending between the knots 174 of the ligature loops 170 of a first pair are shorter in length than the connecting segments 176" of the length of ligature material extending between the first pair and a second, or next adjacent pair of ligature loops. Ligature supply 114 includes spool 172 mounted on mounting bars 189 of an interchangeable adapter 187.

Figure 12:
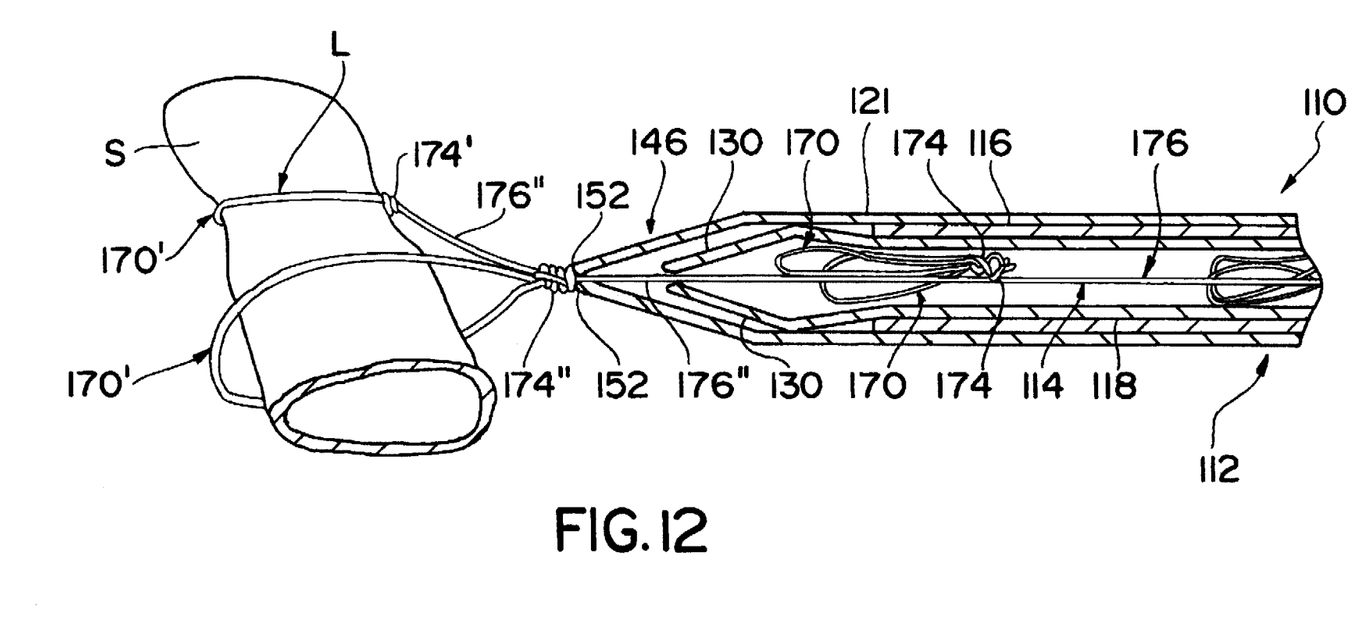
FIG. 12 is a broken side view, partly in section, illustrating use of the ligature supply of FIG. 11 to form a ligature.

Use of a ligating instrument 110 incorporating the ligature supply 114 is illustrated in FIG. 12 wherein the ligating instrument 110 includes an instrument body 112 that is similar to the instrument body 12 but does not include an integral cutter. A first ligature loop 170' of the forward pair of ligature loops is withdrawn through the distal end of the instrument body as described above and is placed around anatomical structure S. Pusher 121 is moved distally relative to actuating member 116 and jaw member 118 to engage the knot 174' of the first ligature loop 170'. The knot 174' cannot pass proximally between the pusher tips 152 since the pusher end 146 is in the closed position, the jaws 130 also being in the closed position due to constraint by actuating member 116. Pusher 121 is moved distally toward anatomical structure S and relative to the connecting segment 176" extending between the first ligature loop 170' and the second ligature loop 170' of the forward pair, the second loop 170' remaining within the instrument body. Once the first ligature loop 170' has been contracted around the anatomical structure S to form a ligature L, the second ligature loop 170' of the forward pair is withdrawn through the distal end of the instrument body and is positioned around the anatomical structure S. FIG. 12 illustrates the second ligature loop 170' positioned around the anatomical structure and connected to the ligature L formed with the first ligature loop by the lo connecting segment 176" extending between the first and second ligature loops 170'. Pusher 121 is moved distally relative to the actuating member 116 and jaw member 118 to engage knot 174' of the second ligature loop 170'. Pusher 121 is moved distally toward anatomical structure S to move the knot 174' of the second ligature lop distally relative to the connecting segment 176" extending between the second ligature lop 170' and the next pair of ligature loops within the instrument body. In this manner, the second ligature loop is contracted around the anatomical structure S to form a second ligature. The length of ligature material 176 is cut proximally of the second ligature with the use of a separate cutting instrument. Accordingly, both the first and second ligature loops 170' of the forward pair will be tightened around the anatomical structure S to form two ligatures for redundant securement or protection as is particularly desirable when ligating a pulsating artery where peristaltic action can tend to displace or loosen a ligature.

The instrument bodies of the ligating instruments according to the present invention can be made of any desirable medical-grade materials, such as stainless steel, to be reusable or to be disposable for single patient use. The jaws can have any desirable configuration including closed or substantially closed configurations defining a hollow interior in the closed position as well as open configurations allowing access to the interior of the jaws in the closed position. The jaws can be formed integrally, unitarily with the body of the jaw member or separately therefrom. The instrument body can be provided with or without a cutter depending on procedural use. The instrument bodies can include various handles, including pistol grip structure. Where the handles include pivotable handgrips, both handgrips can be movable or pivotable or one of the handgrips can be movable or pivotable while the other handgrip remains stationary or fixed. Depending on the design of the instrument bodies, only slight movement of one or more of the elongate members is necessary for movement of the jaws and pusher end between the open and closed positions. The pusher end 46 can have various configurations including closed or substantially closed configurations as well as open configurations allowing access to the interior of the pusher end in the closed position. The ligating instrument can be designed without a separate jaw member in which case the pusher can function as the jaw member to selectively prevent and permit withdrawal of the ligature loops from the instrument body. For example, the pusher can be moved proximally and distally relative to the actuating member to move the pusher between the open and closed positions to selectively perm it passage of the ligature loops between the pusher tips and to selectively prevent passage of the ligature loops between the pusher tips during use. The operating member defined by the pusher can be operated separately from the handle or the pusher can be connected with the handle of the instrument body to be operated thereby. The pusher can be designed to be rotated by the hand grasping the handle for longitudinal movement to contract the ligature loops. For example, an external surface of the pusher can be threaded and received in an annular collar at the proximal end of the pusher for longitudinal movement of the pusher in response to rotation of the collar. With the addition of a separate pusher, the same instrument as that disclosed in applicant's prior application filed Sep. 15, 1995 and incorporated herein by reference can be used to push a knotting element of a ligature loop to contract the ligature loop around anatomical structure to form a ligature. The ligature supplies can be mounted on the instrument bodies in many various ways and at various locations to be operated by the hand grasping the handle. Where more than one ligature loop is positioned around the anatomical structure, the ligature loops can be tightened together or sequentially one at a time. Various types of knotting elements can be utilized for the movable knotting elements of the ligature supplies, including the various knotting elements disclosed in the prior applications incorporated herein by reference. Where the knotting elements are fixable to the ligature material to secure the ligatures as disclosed in the prior applications, the distal end of the instrument body can be operable to fix the knotting elements to the ligature material. The knotting elements can be made of any suitable bioabsorbable or non-bioabsorbable materials. Where bioabsorbable materials are utilized for the knotting elements and/or the ligature material, the materials selected should have rates of absorption to ensure healing of the anatomical structure prior to absorption of the materials to an insubstantial dimension. A variety of ligature supplies can be made available to the surgeon for selection of the optimal ligature supply for the procedure being performed. The ligating instruments are useable in single puncture or multiple puncture endoscopic procedures, and the various instruments utilized in the ligating procedures described herein can be introduced at an internal operative site through the same or different endoscopic portals.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A ligating instrument for forming ligatures in anatomical structure at an internal operative site in the body comprising an elongate instrument body having a distal end for being introduced at the operative site, a proximal end for being disposed externally of the body and a lumen between said distal and proximal ends;

a ligature supply including a plurality of preformed, contractible ligature loops of filamentous ligature material received within said lumen, said ligature loops being withdrawable from said distal end of said instrument body for positioning around anatomical structure and having knotting elements movable along said ligature material in a direction to contract said ligature loops around the anatomical structure, each of said ligature loops including a loop segment of said ligature material extending continuously from one of said knotting elements and back to said one knotting element to form a closed loop, said ligature loops being connected to one another by connecting segments of said ligature material extending between said ligature loops; and an operating member carried by said instrument body and operable from said proximal end of said instrument body for moving said knotting elements in said direction to contract said ligature loops around the anatomical structure to form ligatures.

2. A ligating instrument as recited in claim 1 wherein said connecting segments extend between said knotting elements.

3. A ligating instrument as recited in claim 1 wherein each of said knotting elements is a knot formed of said ligature material.

4. A ligating instrument as recited in claim 3 wherein said loop segments, said knots and said connecting segments are formed from a continuous length of said ligature material.

5. A ligating instrument for forming ligatures in anatomical structure at an internal operative site in the body comprising an elongate member having a distal end for being introduced at the operative site, a proximal end for being disposed externally of the body and a lumen between said distal and proximal ends;

a plurality of preformed, contractible ligature loops of filamentous ligature material received within said lumen, said ligature loops being withdrawable from said distal end of said elongate member for positioning around anatomical structure and having knotting elements movable along said ligature material in a direction to contract said ligature loops around the anatomical structure, said elongate member including jaws at said distal end movable from a closed position wherein said ligature loops cannot pass through said jaws to an open position wherein said ligature loops can pass through said jaws for withdrawal from said distal end of said elongate member; and an operating member carried by said elongate member and operable from said proximal end of said elongate member for moving said knotting elements in said direction to contract said ligature loops around the anatomical structure to form ligatures, said operating member being movable longitudinally along said elongate member and relative to said ligature material for moving said knotting elements distally along said ligature material in the direction of the anatomical structure, said operating member including a distal tip disposed around said ligature material and movable from a tip closed position in which said knotting elements cannot pass through said tip to a tip open position in which said knotting elements can pass through said tip for withdrawal of said ligature loops from said distal end of said elongate member.

6. A ligating instrument as recited in claim 5 wherein said tip is normally disposed in said tip closed position and is moved to said tip open position by engagement of said tip by said jaws.

7. A ligating instrument as recited in claim 6 wherein said jaws are normally disposed in said open position and further including an actuating member carried by said elongate member for maintaining said jaws in said closed position and for selectively releasing said jaws for movement to said open position.

8. A ligating instrument for forming ligatures in anatomical structure at an internal operative site in the body comprising an elongate member having a distal end for being introduced at the operative site, a proximal end for being disposed externally of the body and a lumen between said distal and proximal ends;

a plurality of preformed, contractible ligature loops of filamentous ligature material received within said lumen, said ligature loops being withdrawable from said distal end of said elongate member for positioning around anatomical structure and having knotting elements movable along said ligature material in a direction to contract said ligature loops around the anatomical structure;

an operating member carried by said elongate member and operable from said proximal end of said elongate member for moving said knotting elements in said direction to contract said ligature loops around the anatomical structure to form ligatures; and a cutter carried by said elongate member for cutting said ligature material proximally of ligatures formed with said ligature loops.

9. A ligating instrument as recited in claim 8 wherein said cutter is disposed within said elongate member.

10. A ligating instrument for forming ligatures in anatomical structure at an internal operative site in the body comprising an elongate member having a distal end for being introduced at the operative site, a proximal end for being disposed externally of the body and a lumen between said distal and proximal ends;

a plurality of preformed contractible ligature loops of filamentous ligature material received within said lumen, said ligature loops being withdrawable from said distal end of said elongate member for positioning around anatomical structure and having knotting elements movable along said ligature material in a direction to contract said ligature loops around the anatomical structure;

an operating member carried by said elongate member and operable from said proximal end of said elongate member for moving said knotting elements in said direction to contract said ligature loops around the anatomical structure to form ligatures; and a spool at said proximal end of said elongate member for moving said ligature material distally relative to said elongate member for withdrawal of said ligature loops from said distal end of said elongate member, said spool being rotatable to wind and unwind said ligature material thereon.

11. A ligating instrument for forming ligatures in anatomical structure at an internal operative site in the body comprising an elongate member having a distal end for being introduced at the operative site, a proximal end for being disposed externally of the body and a lumen between said distal and proximal ends;

a plurality of preformed closed, contractible ligature loops of filamentous ligature material received within said lumen, said ligature loops being withdrawable from said distal end of said elongate member for positioning around anatomical structure and having knotting elements formed from said ligature material, said knotting elements being movable along said ligature material in a direction to contract said ligature loops around the anatomical structure; and an operating member carried by said elongate member and operable from said proximal end of said elongate member for moving said knotting elements in said direction to contract said ligature loops around the anatomical structure to form ligatures.

12. A ligating instrument as recited in claim 11 wherein said operating member is movable longitudinally along said elongate member and relative to said ligature material for moving said knotting elements distally along said ligature material in the direction of the anatomical structure.

13. A ligating instrument as recited in claim 12 wherein said operating member includes a pusher having a distal tip disposed around said ligature material and movable from a closed position in which said knotting elements cannot pass through said tip to an open position in which said knotting elements can pass through said tip for withdrawal of said ligature loops from said distal end of said elongate member.

14. A ligating instrument as recited in claim 11 and further including means at said proximal end of said elongate member for moving said ligature material distally relative to said elongate member for withdrawal of said ligature loops from said distal end of said elongate member.

15. A ligating instrument for forming ligatures in anatomical structure at an internal operative site in the body comprising an elongate knot pusher having a distal end for positioning at the operative site, a proximal end for positioning externally of the body and a lumen between said distal and proximal ends, said distal end being movable, from externally of the body, between a closed position and an open position; and a continuous length of filamentous ligature material disposed in said lumen and forming a plurality of interconnected, closed ligature loops and forming a knot for each ligature loop movable longitudinally along said length of ligature material to tighten said ligature loops around anatomical structure to form ligatures, said ligature loops including said knots thereof being withdrawable through said distal end when said distal end is in said open position to deploy said ligature loops at the operative site for positioning around anatomical structure, said knots having a size preventing passage of said knots through said distal end when said distal end is in said closed position, said knot pusher being movable, from externally of the body, along said length of ligature material with said distal end in said closed position to move said knots of said deployed ligature loops along said length of ligature material to tighten said deployed ligature loops around anatomical structure to form ligatures.

16. A ligating instrument as recited in claim 15 and further including an elongate actuating member disposed in said lumen, said knot pusher being movable relative to said elongate actuating member to move said distal end between said open and closed positions.

17. A ligating instrument as recited in claim 16 wherein said distal end of said knot pusher is resiliently biased to be normally disposed in said closed position and said knot pusher is movable longitudinally along said elongate actuating member to move said distal end of said knot pusher from said closed position to said open position.

18. A ligating instrument for forming ligatures in anatomical structure at an internal operative site in the body comprising an elongate knot pusher having a distal end for positioning at the operative site, a proximal end for positioning externally of the body and a lumen between said distal and proximal ends, said distal end being movable, from externally of the body, between a closed position and an open position;

a length of filamentous ligature material disposed in said lumen and forming a plurality of interconnected ligature loops and a knot for each ligature loop movable longitudinally along said length of ligature material to tighten said ligature loops around anatomical structure to form ligatures, said ligature loops including said knots thereof being withdrawable through said distal end when said distal end is in said open position to deploy said ligature loops at the operative site for positioning around anatomical structure said knots having a size preventing passage of said knots through said distal end when said distal end is in said closed position, said knot pusher being movable, from externally of the body, along said length of ligature material with said distal end in said closed position to move said knots of said deployed ligature loops along said length of ligature material to tighten said deployed ligature loops around anatomical structure to form ligatures; and a cutter disposed around said ligature material and operable from externally of the body to cut said length of ligature material proximally of the ligatures.

19. A ligating instrument for forming ligatures in anatomical structure at an internal operative site in the body comprising an elongate knot pusher having a distal end for positioning at the operative site, a proximal end for positioning externally of the body and a lumen between said distal and proximal ends, said distal end being movable from externally of the body, between a closed position and an open position, and a length of filamentous ligature material disposed in said lumen and forming a plurality of interconnected ligature loops and a knot for each ligature loop movable longitudinally along the ligature material to tighten said ligature loops around anatomical structure to form ligatures, said ligature loops being arranged in spaced pairs along said length of ligature material, said ligature loops including said knots thereof being withdrawable through said distal end when said distal end is in said open position to deploy said ligature loops at the operative site for positioning around anatomical structure, said knots having a size preventing passage of said knots through said distal end when said distal end is in said closed position, said knot pusher being movable, from externally of the body, along said length of ligature material with said distal end in said closed position to move said knot of said deployed ligature loops along said length of ligature material to tighten said deployed ligature loops around anatomical structure to form ligatures.

20. A method of forming ligatures in anatomical structures at an internal operative site in the body comprising the steps of providing a ligating instrument including an elongate instrument body having a distal end, a proximal end and a lumen between the distal and proximal ends, a length of filamentous ligature material disposed in the lumen and forming a plurality of interconnected, closed ligature loops and forming a knotting element for each ligature loop movable along the length of ligature material to contract the ligature loops and an operating member movable relative to the length of ligature material to move the knotting elements;

introducing the distal end of the instrument body at the internal operative site;

withdrawing a ligature loop including the knotting element thereof through the distal end of the instrument body to deploy the ligature loop at the operative site;

positioning the deployed ligature loop around anatomical structure;

moving the operating member relative to the length of ligature material from externally of the body to move the knotting element of the deployed ligature loop distally along the length of ligature material in the direction of the anatomical structure to contract the deployed ligature loop around the anatomical structure to form a ligature; and forming another ligature at the operative site with the ligating instrument without withdrawing the ligating instrument from the body.

21. A method of forming ligatures as recited in claim 20 wherein said step of providing includes providing a cutter around the length of ligature material and further including, prior to said step of forming another ligature, the step of cutting the length of ligature material proximally of the ligature.

22. A method of forming ligatures as recited in claim 20 wherein said step of withdrawing includes moving the distal end of the instrument body from a closed position preventing passage of the ligature loop therethrough to an open position permitting passage of the ligature loops including the knotting elements thereof through the distal end of the instrument body.

23. A method of forming ligatures as recited in claim 22 wherein said step of moving includes moving the operating member longitudinally relative to the length of ligature material.

* * * * *